US007557185B2

(12) United States Patent
Cripps et al.

(10) Patent No.: US 7,557,185 B2
(45) Date of Patent: Jul. 7, 2009

(54) MORAXELLA CATARRHALIS PROTEINS

(75) Inventors: Allan W Cripps, Nicholls (AU); Jennelle Kyd, McKellar (AU)

(73) Assignee: Cortecs (OM) Pty Limited, Herdsman (AU)

( * ) Notice: Subject to any disclaimer, the term of this patent is extended or adjusted under 35 U.S.C. 154(b) by 0 days.

(21) Appl. No.: 10/449,735

(22) Filed: Jun. 2, 2003

(65) Prior Publication Data

US 2004/0005328 A1 Jan. 8, 2004

Related U.S. Application Data

(63) Continuation of application No. 09/708,473, filed on Nov. 9, 2000, now abandoned, which is a continuation of application No. PCT/GB99/01473, filed on May 11, 1999.

(30) Foreign Application Priority Data

May 11, 1998 (GB) ................................ 9810084.5

(51) Int. Cl.
C07K 1/00 (2006.01)
(52) U.S. Cl. .................................................. 530/350
(58) Field of Classification Search ............. 424/190.11
See application file for complete search history.

(56) References Cited

U.S. PATENT DOCUMENTS 5,993,826 A * 11/1999 Hansen et al. ........... 424/251.1

FOREIGN PATENT DOCUMENTS

| WO | WO 90/12591 | 11/1990 |
|----|-------------|---------|
| WO | WO 93/03761 | 3/1993 |
| WO | WO 95/09025 | 4/1995 |
| WO | WO 95/31215 | 11/1995 |
| WO | WO 96/12733 | 5/1996 |
| WO | WO 97/32980 | 9/1997 |
| WO | WO 97/41731 | 11/1997 |
| WO | WO 98/06432 | 2/1998 |
| WO | WO 00/18910 A1 | 4/2000 |
| WO | WO 00/71724 A2 | 11/2000 |

OTHER PUBLICATIONS

Bartos et al. ,Journal of Infectious Diseases, vol. 158, No. 4, Oct. 1988.*
Lazar et al, Molecular and Cellular Biology, 1988, vol. 8, pp. 1247-1252.*
Burgess et al. , J of Cell Biology, 1990 vol. 111, pp. 2129-2138.*
Rudikoff et al , Proc Natl Acad Sci USA 1982 vol. 79 p. 1979.*
Murphy and Bartos (Infection and Immunity, 57(10):2938-2941 Oct. 1989).*
Greenbaum et al, Journal of Molecular Recognition, 20(2):75-82, 2007.*
Greenspan et al, Nature Biotechnology 17:936-937, 1999.*
Campbell, Monoclonal Antibody, Elsveier 1984, ch 1.*
Bartos, L.C., and Murphy, T.F., "Comparison of the Outer Membrane Proteins of 50 Strains of *Branhamella catarrhalis*," *J. Infect. Dis.* 158:761-765, University of Chicago Press (1988).
Brusic, V., et al., "Prediction of MHC class II-binding peptides using an evolutionary algorithm and artificial neural network," *Bioinformatics* 14:121-130, Oxford University Press (1998).
Chapman, A.J., et al., "Development of Bactericidal Antibody During *Branhamella catarrhalis* Infection," *J. Infect. Dis.* 151:878-882, University of Chicago Press (1985).
Dougall, W.C., et al., "Antibody-structure-based design of pharmacological agents," *Trends Biotechnol.* 12:372-379, Elsevier Science Publishers (1994).
Faden, H., et al., "Immune Response to Outer Membrane Antigens of *Moraxella catarrhalis* in Children with Otitis Media," *Infect. Immun.* 60:3824-3829, American Society for Microbiology (1992).
Georges, B., et al., "Analysis of peptides associated with class II MHC molecules HLA-DR3: implication for prediction of peptides useful for vaccines," *C.R. Acad. Sci.* 319:1119-1125, Éditions Scientifiques et Médicales Elsevier (1996).
Gershoni, J.M., et al., "Combinatorial libraries, epitome structure and the prediction of protein conformations," *Immunol. Today* 18:108-110, Elsevier Science Publishers (1997).
Hammer, J., et al., "HLA Class II Peptide Binding Specificity and Autoimmunity," *Adv. Immunol.*, 66:67-100, Academic Press (1997).
Klein, J.O., "Otitis Media," *Clin. Infec. Dis.* 19:823-833, The University of Chicago Press (1994).
Kyd, J.M., et al., "Enhanced Respiratory Clearance of Nontypeable *Haemophilus influenzae* following Mucosal Immunization with P6 in a Rat Model," *Infect. Immun.* 63:2931-2940, American Society for Microbiology (1995).
Matsudaira, P., "Sequence from Picomole Quantities of Proteins Electroblotted onto Polyvinylidene Difluoride Membranes," *J. Biol. Chem.* 262:10035-10038, The American Society of Biological Chemists, Inc. (1987).
Morrison, S.L., et al., "Chimeric human antibody molecules: Mouse antigen-binding domains with human constant region domains," *Proc. Natl. Acad. Sci. USA* 81:6851-6855, National Academy of Sciences (1984).
Murphy, T.F., "*Branhamella catarrhalis*: Epidemiology, Surface Antigenic Structure, and Immune Response," *Microbiol. Rev.* 60:267-279, American Society for Microbiology (1996).
Myers, L.E., et al., "The Transferrin Binding Protein B of *Moraxella catarrhalis* Elicits Bactericidal Antibodies and Is a Potential Vaccine Antigen," *Infect. Immun.* 66; 4183-4192, American Society for Microbiology (Sep. 1998).
Nicotra, B., et al., "*Branhamella catarrhalis* as a Lower Respiratory Tract Pathogen in Patients With Chronic Lung Disease," *Arch. Intern. Med.* 146:890-893, American Medical Association (1986).
Schryvers, A.B., and Lee, B.C., "Comparative analysis of the transferrin and lactoferrin binding proteins in the family Neisseriaceae," *Can. J. Microbiol.* 35:409-415, National Research Council Canada (1989).

(Continued)

*Primary Examiner*—Patricia A Duffy
(74) *Attorney, Agent, or Firm*—Sterne, Kessler, Goldstein & Fox P.L.L.C.

(57) ABSTRACT

Novel antigens of *B. catarrhalis* are provided, together with their use in vaccines as well as methods of diagnosing and/or detection.

7 Claims, 4 Drawing Sheets

OTHER PUBLICATIONS

Figure 1:
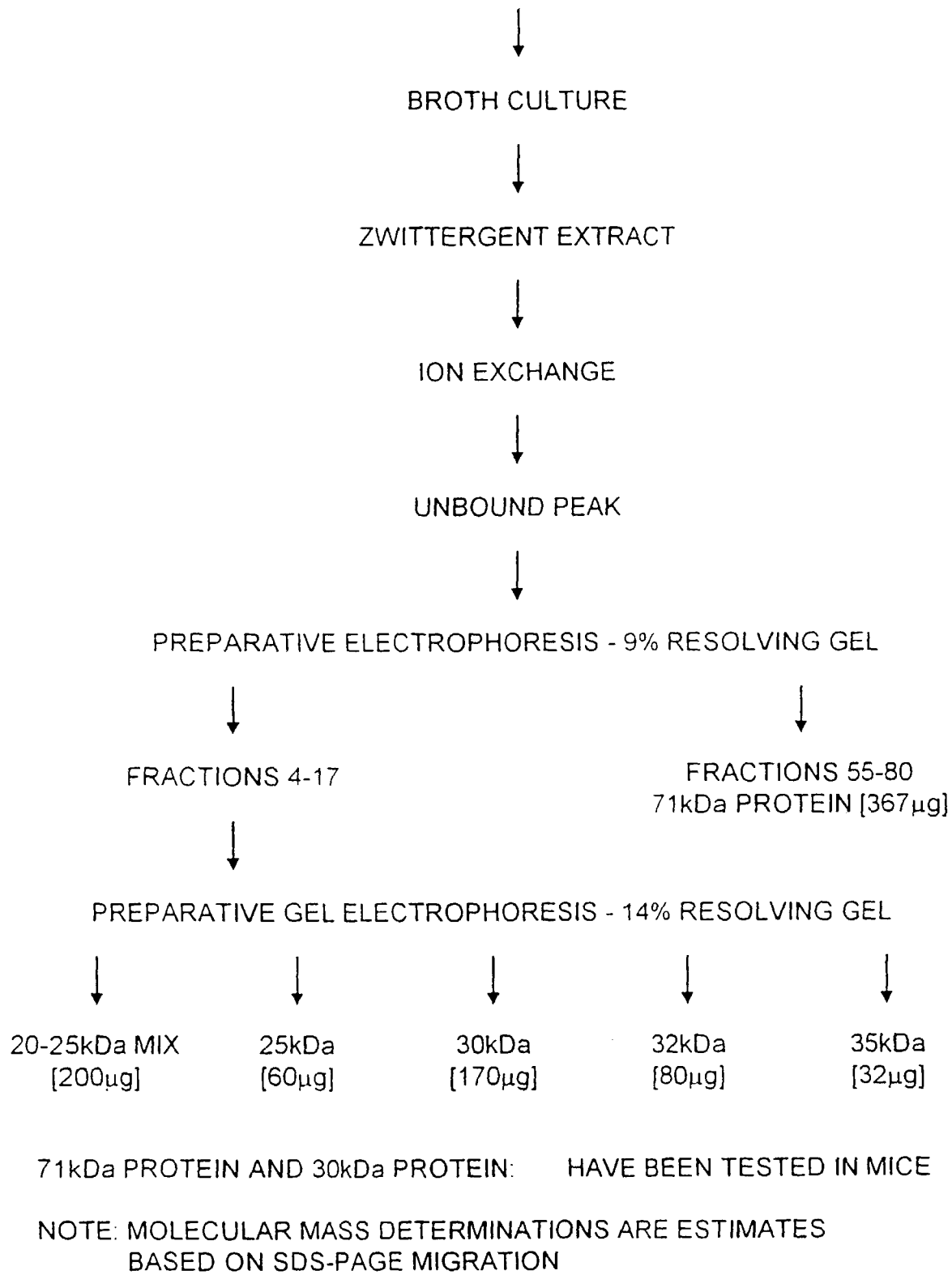

Sethi, S., et al., "Serum Antibodies to Outer Membrane Proteins (OMPs) of *Moraxella* (*Branhamella*) *catarrhalis* in Patients with Bronchiectasis: Identification of OMP B1 as an Important Antigen," *Infect. Immun.* 63:1516-1520, American Society for Microbiology (1995).

Stenfors, L.E., and Räisänen, S., "Secretory IgA-, IgG- and C3b-coated Bacteria in the Nasopharynx of Otitis-Prone and Non-Otitis-Prone Children," *Acta Otolaryngol.* (*Stockh*) 113:191-195, Scandinavian University Press (1993).

Takeda, S-I., et al., "Construction of chimaeric processed immunoglobuin genes containing mouse variable and human constant region sequences," *Nature* 314:452-454, Macmillan Journals (1985).

Verghese, A., et al., "Randomized Comparative Study of Cefixime versus Cephalexin in Acute Bacterial Exacerbations of Chronic Bronchitis," *Antimicrob. Agents Chemother.* 34:1041-1044, American Society for Microbiology (1990).

Yu, R-H., and Schryvers, A.B., "The interaction between human transferrin and transferrin binding protein 2 from *Moraxella* (*Branhamella*) *catarrhalis* differs from that of other human pathogens," *Microbial Pathogenesis* 15:433-445, Academic Press Limited (1993).

STNEasy, Database CAplus, Accession No. 1997:103995, English language abstract for Georges, B., et al., "Analysis of peptides associated with class II MHC molecules HLA-DR3: implication for prediction of peptides useful for vaccines," *C.R. Acad. Sci.* 319:1119-1125, Éditions Scientifiques et Médicales Elsevier (1996).

Kyd, J., et al., "Investigation of mucosal immunisation in pulmonary clearance of *Moraxella* (*Branhamella*) *catarrhalis*," *Vaccine* 18: 398-406, Elsevier Science Ltd. (Oct. 1999).

* cited by examiner

SDS-PAGE SHOWING PURIFIED PROTEINS RANGING FROM 23 kDa TO 71 kDa FOLLOWING SILVER STAINING.

ENHANCED CLEARANCE OF B CATARRHALIS IN MICE MUCOSALLY IMMUNIZED WITH PROTEIN ANTIGENS (% COMPARISON WITH NON-IMMUNE MICE)

SEQUENCE LISTING

<160> NUMBER OF SEQ ID NOS: 9

<210> SEQ ID NO 1
<211> LENGTH: 31
<212> TYPE: PRT
<213> ORGANISM: Branhamella catarrhalis

<400> SEQUENCE: 1

Ala Ile Ser Tyr Gly Asn Ser Ala Asp Ala Gln Pro Tyr Val Gly Ala
 1               5                  10                  15

Lys Ile Gly Gln Val Asp Ala Lys Gln Ile Asn Asn Lys Asn Thr
            20                  25                  30

<210> SEQ ID NO 2
<211> LENGTH: 31
<212> TYPE: PRT
<213> ORGANISM: Branhamella catarrhalis

<400> SEQUENCE: 2

Asn Val Val Thr Asn Thr Gly Ala Thr Val Val Asp Gly Thr Arg Thr
 1               5                  10                  15

Ile Phe Ser Thr Leu Val Lys Pro Ala Ala Val Val Ala Ala Val
            20                  25                  30

<210> SEQ ID NO 3
<211> LENGTH: 21
<212> TYPE: PRT
<213> ORGANISM: Branhamella catarrhalis
<220> FEATURE:
<221> NAME/KEY: SITE
<222> LOCATION: (19)
<223> OTHER INFORMATION: Xaa is any amino acid

<400> SEQUENCE: 3

Thr Pro Thr Val Tyr Gly Lys Ala Phe Leu Thr Ile Asp Ala Asn Asn
 1               5                  10                  15

Thr Asp Xaa Thr Tyr
            20

<210> SEQ ID NO 4
<211> LENGTH: 20
<212> TYPE: PRT
<213> ORGANISM: Branhamella catarrhalis

<400> SEQUENCE: 4

Ala Gly Leu Asp Arg Ser Gly Gln Asp Val Thr Ala Ser Leu Gln Asp
 1               5                  10                  15

Gly Thr Tyr Ala
            20

<210> SEQ ID NO 5
<211> LENGTH: 12
<212> TYPE: PRT
<213> ORGANISM: Branhamella catarrhalis

<400> SEQUENCE: 5

Gly Glu Leu Ser Ser Asn Leu Gln Asp Arg His Lys
 1               5                  10

<210> SEQ ID NO 6
<211> LENGTH: 16
<212> TYPE: PRT

```
<213> ORGANISM: Branhamella catarrhalis

<400> SEQUENCE: 6

Ala Asp Ile His Gly Asn Arg Phe Arg Gly Ser Ala Ala Ile Ala Ser
1               5                   10                  15

<210> SEQ ID NO 7
<211> LENGTH: 6
<212> TYPE: PRT
<213> ORGANISM: Branhamella catarrhalis

<400> SEQUENCE: 7

Asn Phe Glu Tyr Leu Lys
1               5

<210> SEQ ID NO 8
<211> LENGTH: 15
<212> TYPE: PRT
<213> ORGANISM: Branhamella catarrhalis

<400> SEQUENCE: 8

Phe Gly Glu Leu Ser Val Gly Asp Ser His Ser Val Phe Leu Gln
1               5                   10                  15

<210> SEQ ID NO 9
<211> LENGTH: 18
<212> TYPE: PRT
<213> ORGANISM: Branhamella catarrhalis

<400> SEQUENCE: 9

Asp Ala Asp Val Thr Gly Gly Phe Tyr Gly Pro Asn Ala Thr Glu Met
1               5                   10                  15

Gly Gly
```

MORAXELLA CATARRHALIS PROTEINS

CROSS-REFERENCE TO RELATED APPLICATIONS

This application is a continuation of U.S. application Ser. No. 09/708,473, filed on Nov. 9, 2000, now abandoned, which is a continuation of International Application No. PCT/GB99/01473, International Application filed May 11, 1999, which was published in English as WO 99/58563 on Nov. 18, 1999 and which is fully incorporated herein by reference; said applications claim the benefit of the filing date of Great Britain Application GB 9810084.5, filed May 11, 1998.

FIELD OF THE INVENTION

The present invention relates to novel proteins from *Branhamella catarrhalis*, DNA sequences encoding such proteins, as well as their use in diagnosis and as the basis for vaccines.

*Branhamella catarrhalis* (also known as *Moraxella catarrhalis*) is a gram-negative aerobic bacterium that causes respiratory tract infections in humans. *B. catarrhalis* can exist as part of the human respiratory tract microflora, particularly in children. The bacterium causes lower respiratory tract infections in adults and otitis media in children (Klein J. O., *Clin. Infect. Dis.,* 19:823-833 (1994); Murphy, T. F., *Microbial. Rev.,* 60:267-279 (1996); Nicotra et al., *Arch. Intern. Med.,* 146:890-893). Approximately 30% of purulent exacerbations in adults with chronic obstructive lung pulmonary disease were by *B. catarrhalis* in one study (Verghese et al., *Antimicrob. Agents Chemother.,* 34:1041-1044 (1990). Studies using cultures of middle ear fluid reveal that 15 to 20% of episodes of otitis media are caused by *B. catarrhalis* (Klein (1994), supra).

Infections caused by *B. catarrhalis* induce an immune response against outer membrane antigens of the bacterium (Chapman et al., *J. Infect. Dis.,* 151:878-882 (1985); Faden et al., *Infect. Immun.,* 60:3824-3829 (1992); Sethi et al., *Infect. Immun.,* 63:1516-1520 (1995)). Antibody to *B. catarrhalis* is present in secretions in the upper respiratory tract (Fadden (1992), supra; Stenfors, L. E. and Raisanen, S., *Acta Otolaryngol.,* 113:191-195 (1993)). Strain-specific mucosal immune response may be important in protection against otitis media caused by *B. catarrhalis* (Faden (1992), supra and Stenfors and Raisanen (1993), supra).

A number of patent publications have disclosed isolated protein d from *B. catarrhalis*, and their potential use as antigens. Examples include WO90/12591, WO93/03761, WO95/09025, WO95/31215, WO96/12733 and WO97/41731.

There is, however, a continuing need to provide a range of antigens from *B. catarrhalis* in order to provide better and more effective vaccines for instance. We have now isolated a range of such proteins which can be used to elicit immune responses, as well as finding use as diagnostic tools.

Thus, in a first aspect, the present invention provides a protein which is a *B. catarrhalis* antigen and which has an apparent molecular mass of about 14 to about 71 kDa, as determined by SDS-PAGE.

In preferred embodiments the protein is one of the following, isolatable from *B. catarrhalis:*

(i) a protein having an apparent molecular mass of about 14 kDa, as determined by SDS-PAGE;

(ii) a protein having an apparent molecular mass of about 14.5 kDa, as determined by SDS-PAGE;

(iii) a protein having an apparent molecular mass of about 15 kDa, as determined by SDS-PAGE;

(iv) a protein having an apparent molecular mass of about 20 kDa, as determined by SDS-PAGE, and having the following N-terminal sequence:

AISYGNSADAQPYVGAKIGQVDAKQINNKNT (SEQ ID NO:1);

(v) a protein having an apparent molecular mass of about 30 kDa, as determined by SDS-PAGE, and having the following N-terminal sequence:

NVVTNTGATVVDGTRTIFSTLVKPAAVVAAV (SEQ ID NO:2);

(vi) a protein having an apparent molecular mass of about 35 kDa, as determined by SDS-PAGE, and having the following N-terminal sequence:

TPTVYGKAFLTIDANNTDXTY (SEQ ID NO:3);

(vii) a protein having an apparent molecular mass of about 44 kDa, as determined by SDS-PAGE, and having the following N-terminal sequence:

AGLDRSGQDVTASLQDGTYA (SEQ ID NO:4);

(viii) a protein having an apparent molecular mass of 71 kDa, as determined by SDS-PAGE, and having the following internal peptide sequences:

Residues 350-361

GELSSNLQDRHK (SEQ ID NO:5)

Residues 366-380

ADIHGNRFRGSAAIAS (SEQ ID NO:6)

Residues 528-233

NFEYLK (SEQ ID NO:7)

Residues 542-556

FGELSVGDSHSVFLQ (SEQ ID NO:8)

Residues 665-682

DADVTGGFYGPNATEMGG (SEQ ID NO:9)

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject. Thus, in the latter case, the protein or polypeptide may be capable of not only generating an antibody response and in addition non-antibody based immune responses.

The skilled person will appreciate that homologues or derivatives of the proteins or polypeptides of the invention will also find use in the context of the present invention, i.e. as antigenic/immunogenic material. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein or polypeptide as described herein is less important than that the homologue or derivative should retain its antigenicity or immunogenicity. However, suitably, homologues or derivatives having at least 60% similarity (as discussed above) with the proteins or polypeptides described herein are provided. Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

Gene cloning techniques may be used to provide a protein of the invention in substantially pure form. These techniques are disclosed, for example, in J. Sambrook et al *Molecular Cloning* 2nd Edition, Cold Spring Harbor Laboratory Press (1989). Thus, the N-terminal sequences of the proteins disclosed herein can in turn be used as the basis for probes to isolate the genes coding for the individual proteins. Thus, in another aspect the present invention provides a nucleic acid molecule comprising or consisting of a sequence which is:

(i) a DNA sequence coding for a protein or polypeptide as described herein or their RNA equivalents;
(ii) a sequence which is complementary to any of the sequences of (i);
(iii) a sequence which has substantial identity with any of those of (i) and (ii);
(iv) a sequence which codes for a homologue, derivative or fragment of a protein as defined herein.

The nucleic acid molecules of the invention may include a plurality of such sequences, and/or fragments. The skilled person will appreciate that the present invention can include novel variants of those particular novel nucleic acid molecules which are exemplified herein. Such variants are encompassed by the present invention. These may occur in nature, for example because of strain variation. For example, additions, substitutions and/or deletions are included. In addition and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention compare when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes designed on the basis of the N-terminal amino acid sequences described herein, genes in *B. catarrhalis* can be identified. They can then be excised using restriction enzymes and cloned into a vector. The vector can be introduced into a suitable host for expression.

Nucleic acid molecules of the present invention may be obtained from *B. catarrhalis* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree. One primer will normally show a high degree of specificity for a first sequence located on one strand of a DNA molecule, and the other primer will normally show a high degree of specificity for a second sequence located on the complementary strand of the DNA sequence and being spaced from the complementary sequence to the first sequence.

Typically primers will be at least 15-25 nucleotides long.

As a further alternative chemical synthesis may be used. This may be automated. Relatively short sequences may be chemically synthesised and ligated together to provide a longer sequence.

The skilled person will recognise that SDS-PAGE determination of molecular mass yields results which are subject to something of the order of ±10% variation. Thus, any apparent molecular weight described herein, which has been so determined will be subject to such variation.

It will be appreciated by the skilled man that fragments of the antigenic proteins of the invention could also be used, with the proviso of course that such fragments retain sufficient antigenicity to be effective. Techniques for screening such fragments are well known to those skilled in the art. Thus, in a second aspect, the present invention provides one or more antigenic fragments of a protein as described herein.

As mentioned above one of the primary uses of the antigens (including antigenic fragments) of the present invention is in eliciting an immune response. Thus, in a third aspect, the present invention provides an immunogenic composition, preferably a vaccine composition, which comprises one or more of the antigens of the invention (including antigenic fragments). The composition can be formulated with standard pharmaceutical carriers, excipients, diluents and the like. In addition, it can include one or more adjuvants, useful in boosting any immune response. The vaccine compositions of the invention can include one or more adjuvants. Examples of adjuvants well known in the art include inorganic gels such as aluminium hydroxide or water-in-oil emulsions such as incomplete Freund's adjuvant. Other useful adjuvants will be well known to the skilled man.

In a fourth aspect, the present invention provides the use of one or more proteins as defined herein, or one or more antigenic fragments thereof in the preparation of an immunogenic composition. Preferably, the immunogenic composition is a vaccine. In preferred embodiments, the vaccine is for use in the prophylaxis or treatment of respiratory infection or the prophylaxis or treatment of otitis media.

In particular, one or more of the following proteins, homologues, derivatives or one or more antigenic fragments thereof, is/are used in the preparation of the immunogenic composition:

(i) a protein having an apparent molecular mass of about 14 kDa, as determined by SDS-PAGE;
(ii) a protein having an apparent molecular mass of about 14.5 kDa, as determined by SDS-PAGE;
(iii) a protein having an apparent molecular mass of about 15 kDa, as determined by SDS-PAGE;
(iv) a protein having an apparent molecular mass of about 20 kDa, as determined by SDS-PAGE, and having the following N-terminal sequence:

AISYGNSADAQPYVGAKIGQVDAKQINNKNT (SEQ ID NO:1);

(v) a protein having an apparent molecular mass of about 30 kDa, as determined by SDS-PAGE, and having the following N-terminal sequence:

NVVTNTGATVVDGTRTIFSTLVKPAAVVAAV (SEQ ID NO:2);

(vi) a protein having an apparent molecular mass of about 35 kDa, as determined by SDS-PAGE, and having the following N-terminal sequence:

TPTVYGKAFLTIDANNTDXTY (SEQ ID NO:3);

(vii) a protein having an apparent molecular mass of about 44 kDa, as determined by SDS-PAGE, and having the following N-terminal sequence:

AGLDRSGQDVTASLQDGTYA (SEQ ID NO:4);

(viii) a protein having an apparent molecular mass of 71 kDa, as determined by SDS-PAGE, and having the following internal peptide sequences:

Residues 350-361

GELSSNLQDRHK (SEQ ID NO:5)

Residues 366-380

ADIHGNRFRGSAAIAS (SEQ ID NO:6)

Residues 528-233

NFEYLK (SEQ ID NO:7)

Residues 542-556

FGELSVGDSHSVFLQ (SEQ ID NO:8)

Residues 665-682

DADVTGGFYGPNATEMGG (SEQ ID NO:9)

The antigenic proteins, derivatives, homologues or fragments thereof, described herein can be provided alone, as a purified or isolated preparation, or as part of a mixture with other *B. catarrhalis* antigenic proteins.

In a fifth aspect therefore, the invention provides an antigen composition comprising one or more of the proteins of the invention, one or more homologues or derivatives or one or more antigenic fragments thereof, optionally together with at least one other *B. catarrhalis* antigen, or one or more antigenic fragments thereof.

Additionally, the proteins of the present invention, or antigenic fragments thereof, can be used in raising or selecting antibodies.

In a further aspect, therefore, the present invention provides antibodies raised against at least one protein of the invention, or against one or more antigenic fragments thereof. Preferred antibodies bind specifically to proteins of the present invention and can therefore be used to purify such proteins (e.g. they may be immobilised and used to bind to proteins of the present invention. The proteins may then be eluted by washing with a suitable eluent under appropriate conditions.)

Antibodies within the scope of the present invention may be monoclonal or polyclonal.

Polyclonal antibodies can be raised by stimulating their production in a suitable animal host (e.g. a mouse, rate, guinea pig, rabbit, sheep, goat or monkey) when a protein of the present invention is injected into the animal. If desired, an adjuvant may be administered together with a protein of the present invention. Well-known adjuvants such as those described above may be used. The antibodies can then be purified by virtue of their binding to a protein of the present invention.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins of the present invention. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, F(ab')$_2$ and Fv fragments, which are discussed in Riott et al [supra]. Fv fragments can be modified to produce a synthetic construct known as a single chain Fv (scFv) molecule. This includes a peptide linker covalently joining $V_H$ and $V_L$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in PNAS, 81, 6851-6855 (1984) and by Takeda et al in Nature 314, 452-454 (1985).

Synthetic constructs also include molecules comprising an additional moiety that provides the molecule with some desirable property in addition to antigen binding. For example the moiety may be a label (e.g. a fluorescent or radioactive label).

The antibodies or derivatives thereof of the present invention will also find use in detection/diagnosis of *B. catarrhalis*.

In a seventh aspect the present invention provides a method of detecting and/or diagnosing *B. catarrhalis* which comprises:

(a) bringing into contact one or more antibodies of the invention, with a sample to be tested; and
(b) detecting the presence of one or more of the antigenic proteins of the invention, or one or antigenic fragments thereof.

Alternatively, the antigenic proteins of the present invention can be used to detect antibodies against *B. catarrhalis*, which may be present in a biological sample obtained from a subject. Thus, in yet a further aspect, the present invention provides a method of detecting and/or diagnosing *B. catarrhalis* which comprises:

(a) bringing into contact one or more antigenic proteins of the invention, or one or more antigenic fragments thereof, as defined herein, or in immunogenic composition of the invention with a sample to be tested; and
(b) detecting the presence of antibodies to *B. catarrhalis*.

In an additional aspect, the invention provides the use of an antigenic protein, antigenic fragment thereof or immunogenic composition of the present invention in detecting and/or diagnosing *B. catarrhalis*. Preferably, the detecting and/or diagnosing is carried out in vitro.

The antigenic proteins, antigenic fragments thereof or antigen composition of the invention can be provided as part of a kit for use in in vitro detection and/or diagnosis of *B. catarrhalis*. Thus, in another aspect, the present invention provides a kit for use in the detection and/or diagnosis of *B. catarrhalis* comprising at least one antigenic protein, antigenic fragment thereof, antigen composition of the invention or at least one antibody of the invention.

As discussed above, the antigenic proteins or antigenic fragments thereof can be used to induce an immune response against *B. catarrhalis*. Thus, in a further aspect, the present invention provides the use of the antigen, a fragment thereof or an antigenic composition of the invention in medicine.

In additional aspects, the present invention provides:

(a) the use of antigenic protein, an antigenic fragment thereof or an immunogenic composition, as described herein in inducing an immune response in a subject;
(b) a method for the treatment of prophylaxis of respiratory infection in a subject, which comprises the step of administering to the subject an effective amount of at least one protein, at least one antigenic fragment thereof or an immunogenic composition of the invention, preferably as a vaccine; and
(c) a method for the treatment or prophylaxis of otitis media in a subject, which comprises the step of administering to the subject an effective amount of at least one protein, at least one antigenic fragment thereof or an immunogenic composition of the invention, preferably as a vaccine.

A convenient method for production of the antigenic protein described herein (or indeed fragments thereof) is by the use of recombinant DNA techniques.

Figure 2:
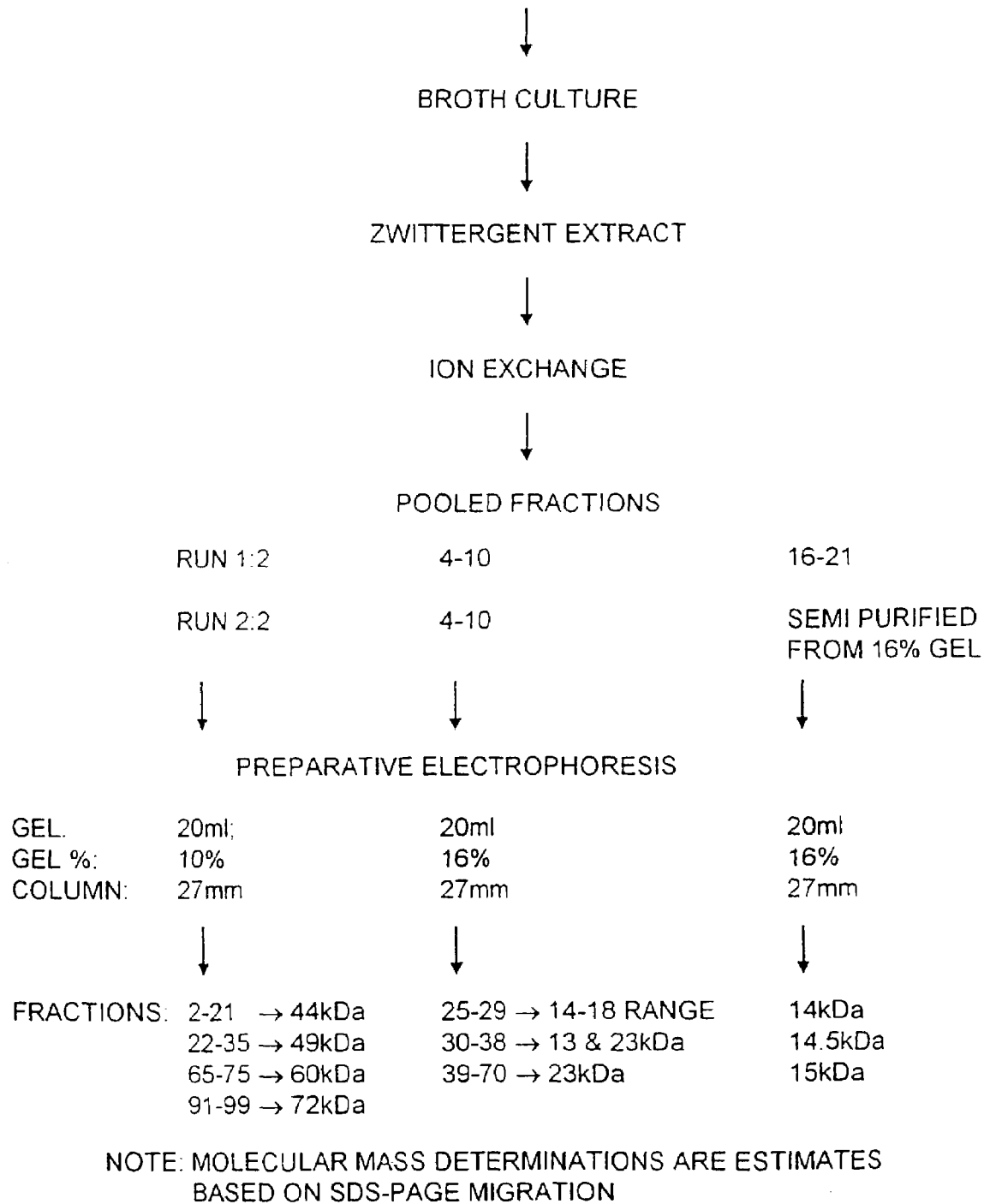
Figure 3:
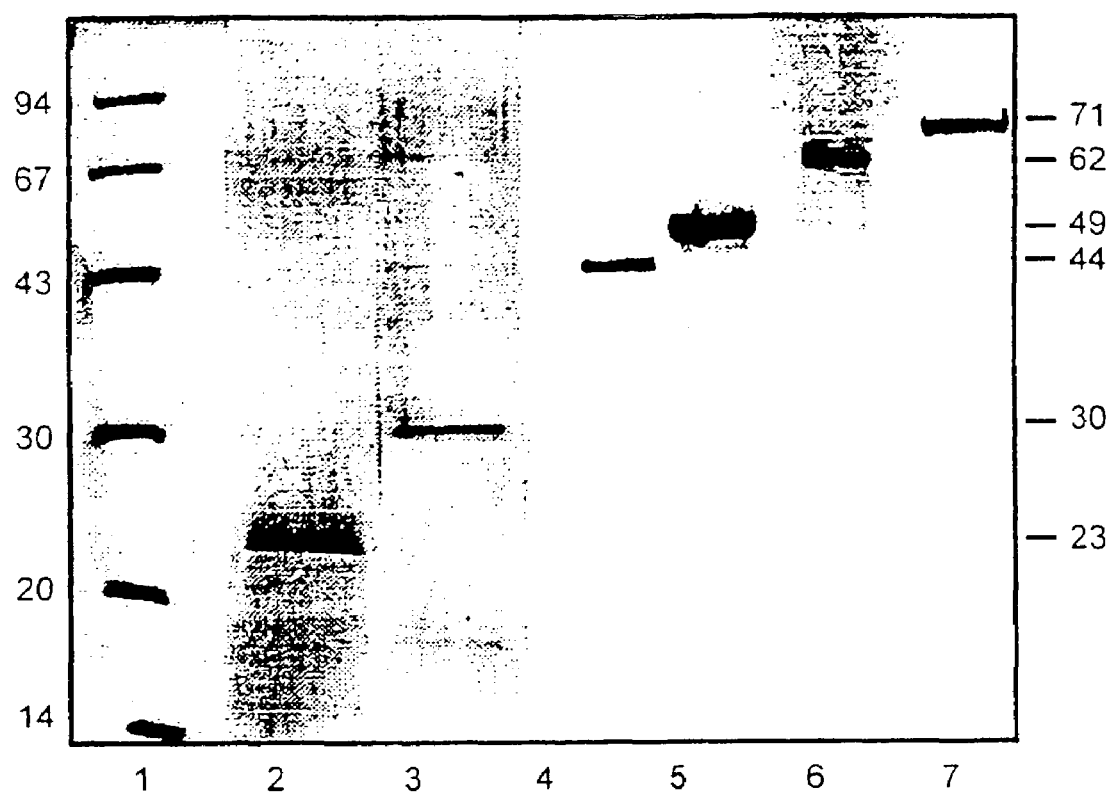
Figure 4:
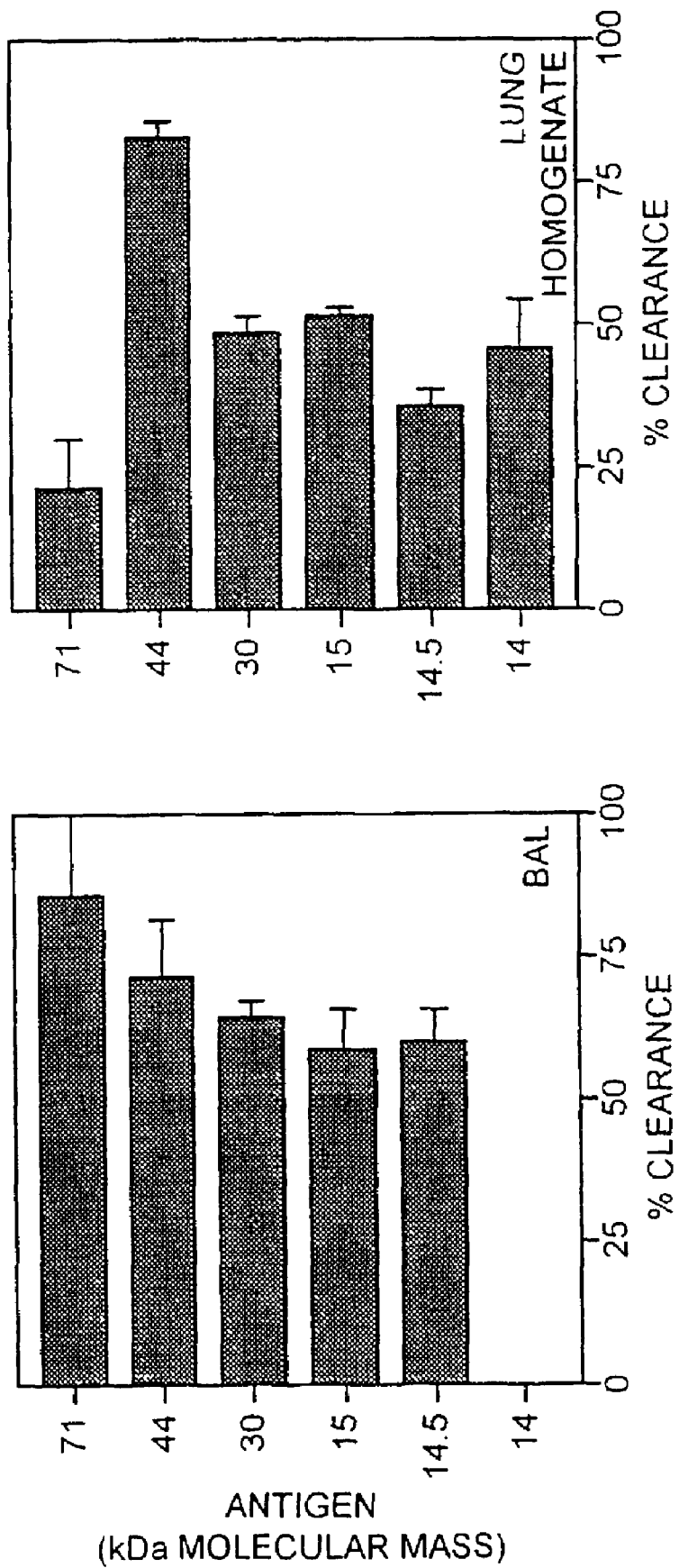

The present invention will now be described with reference to the following examples, which should not be construed as in any way limiting the invention. The examples refer to the figures in which:

FIG. 1: shows a flow diagram representation for the isolation of the 30 kDa and 71 kDa proteins described herein;

FIG. 2: shows a flow diagram representation for the isolation of the 14 kDa, 14.5 kDa and 15 kDa proteins described herein;

FIG. 3: shows an SDS-PAGE gel showing purified proteins following silver staining; and FIG. 4: shows clearance rate data for *B. catarrhalis* infected mice with or without immunisation with antigens of the invention.

EXAMPLE 1

Purification of Proteins (i) 30 kDa and 71 kDa 20 mls Brain heart infusion broth were inoculated with 4-5 colonies of *B. catarrhalis* K65 strain (a clinical isolate from sputum recovered at the Sir Charles Gardiner Hospital, Perth, Australia; strain K65 produces a β-lactamase) and incubated overnight at 37° C. in a shaker incubator. 2 mls of the culture were added to each of 4×500 ml flasks of BHI broth and incubated overnight at 37° C. in a shaker incubator. The bacteria were pelleted and washed three times in PBS at 10,000 rpm for 15 mins at 4° C. in a Beckman JA-2 centrifuge using a JA-14 rotor. The proteins were extracted using a Zwittergent extraction and ethanol precipitation method with the exception that there was no pH adjustment after the addition of sodium acetate/β-mercaptoethanol. The final product was dialysed against distilled water yielding 40 mls at 15.35 mg/ml, a total of 614 mg protein. The preparations were freeze dried.

The protein extract was resuspended to approx. 60 mg/ml in Buffer A (25 mM tris-HCl, pH 8.1) before loading into a BioRad Q2 ion-exchange column. 1 ml aliquots were loaded on each run. The column was washed with Buffer A for 5 mins at 1 ml/min. The proteins were eluted using a combination of continuous and step gradients from 100% Buffer A to 100% Buffer B (25 mM Tris-HCl+0.5M NaCl, pH 8.1) over 5-10 mins. The gradient was followed by a 4 min wash with 100% Buffer B followed by a 1 min wash with 100% Buffer A. Fractions 2, 3 and 4 were pooled, desalted on a PD-10 column to change to diluted Tris buffer then freeze-dried.

The volume was adjusted to 600 μl with distilled water, mixed with 2.4 ml reducing buffer (62.5 mM Tris, pH6.8, 10% v/v glycerol, 2% w/v SDS, 5% v/v β-mercaptoethanol, $1.2 \times 10^{-3}$% w/v bromophenol blue) and incubated at 37° C. for 30 mins. Preparative SDS-PAGE to purify proteins was performed using the Bio-Rad Model 491 Prep Cell using a 40 ml 9% T-1.42% C acrylamide/BIS (N,N'-methylenebis acrylamide) separating gel with a 10 ml 4% t-0.36% C acrylamide/BIS stacking gel polymerized in a 37 mm (internal diameter [i.d.]) column. Fractions were eluted from the column with 0.025M Tris-HCl, were concentrated by lyophilization and analysed for protein content by analytical SDS-PAGE. The 71 kDa protein was in fractions 57-80. These were pooled, freeze-dried and reconstituted in 2.5 ml distilled water. The preparation was desalted by buffer exchange using diluted PBS and reconcentrated so that the concentration of PBS buffering the protein was isotonic.

From this same preparative cell run, fractions 26-34, containing 55-65 kDa proteins, and fractions 4-17, containing 20-35 kDa proteins, were also pooled. Fractions 4-17 were further purified using a 145 T-1.42% C acrylamide/BIS separating gel with a 4% T-0.36% C acrylamide/BIS stacking gel (see FIG. 1 flow diagram). Fractions were assessed for protein content as described above, appropriate fraction ranges pooled and purified proteins desalted and concentrated.

(ii) Purification of Other Proteins

20mls Brain heart infusion broth were inoculated with 4-5 colonies of *B. catarrhalis* K65 strain and incubated overnight at 37° C. in a shaker incubator. 2 mls of the culture were added to each of 4×500 ml flasks of BHI broth and incubated overnight at 37° C. in a shaker incubator. The bacteria were pelleted and washed three times in PBS at 10,000 rpm for 15 mins at 4° C. in a Beckman JA-2 centrifuge using a JA-14 rotor. The proteins were extracted using a Zwittergent extraction and ethanol precipitation method with the pH of sodium acetate/β-mercaptoethanol adjusted to pH 4.

The protein extract was resuspended to approx. 60 mg/ml in Buffer A before loading onto a BioRad Q2 ion-exchange column using the protocol described above. Peaks from the column were assessed for protein content, appropriate fractions pooled and subjected to further purification using preparative gel electrophoresis (using columns as indicated in FIG. 2 and protocols as described above). All protein purifications that involved preparative electrophoresis using SDS had this detergent removed by precipitation with potassium phosphate.

Results

Several proteins were purified from other membrane extracts of *B. catarrhalis* in quantities ranging from 10 μg to 300 μg from a single extraction procedure. FIG. 3 shows an analytical SDS-PAGE analysis of proteins ranging from 23 to 71 kDa.

Amino Acid Sequence Identification

N-terminal Sequencing

This can be carried out according to protocols supplied by Applied Biosystems protocols. However, in addition, the skilled person can also carry out such sequencing according to the methods described in Matsudaira, *J.Biol. Chem.*, 262: 10035-10038 (1997).

Internal Peptide Sequencing

Sequencing was carried out using the SDS-PAGE compatible S-2-carboxamidothylation method. The alkylation reaction was performed on the protein in a solution of 10% glycerol (vol/vol), 5% (wt/vol) SDS, 0.025 M TrisHCl, 100 mM 1,4-DTT, pH 8.3. The protein was reduced initially by incubating this mixture at 90° C. for 15 minutes. The sample was then cooled to 37° C., acrylamide added to a final concentration of 2M and the mixture incubated under argon with light excluded for 30 to 60 minutes. SDS reducing buffer was added, the sample subjected to SDS-PAGE, the protein was visualised by coomassie staining and excised from the gel. This procedure was performed on a 71 kDa protein that was unable to be N-terminally sequenced.

EXAMPLE 2

Immunisation Regimes

Intra-Peyer's patch (IPP) immunisation was a modification of a method described for rats (Kyd et al, *Infect. Immun.*, 63:2931-2940 (1995)). The immunisation innoculum was prepared by emulsifying the protein with incomplete Freund's adjuvant (IFA) (Sigma, St Louis, Mich.) in a 1:1 ratio to enable dosages ranging from 2.5 μg to 10 μμg. Specific pathogen free (SPF) male BALB/c mice aged 6 to 8 weeks, maintained under SPF conditions were anaesthetised by a subcutaneous injection of 0.25 ml ketamine/xylazine in PBS (5 mg/ml ketamine hydrochloride [Troy Laboratories, Smithfield, NSW, Australia]; 2 mg/ml xylazine hydrochloride [Bayer, Pymble, NSW, Australia]). The small intestine was exposed through a 1 cm midline incision in the abdominal wall and approximately 1 μl volumes inoculum were delivered subserosally to each Peyer's patch using a 26G needle. The intestines were rinsed with sterile PBS and the abdominal cavity sutured. Sham-immunised mice were subjected to the same surgical procedure with injection of an emulsion of IFA and PBS.

An intra tracheal (IT) boost was given on day 14 post-IPP. Mice were sedated by intravenous saffan anaesthesia (0.15 ml; 20 mg alphadone in PBS/kg body weight; Pitman-Moore, Nth Ryde, NSW, Australia). A 20 μl volume of protein in PBS (the same amount that was administered IPP) was delivered into the lungs via a 22.5G catheter (Terumo, Tokyo, Japan) inserted orally into the trachea. The inoculum was dispersed with two 0.3 ml volumes of air.

Bacterial Challenge

*B. catarrhalis* was grown overnight on plates of brain heart infusion (BHI) agar supplemented with 50 ml per litre of defibrinated horse blood (Amadeus International, Brooklyn, Vic, Australia). Plates were incubated overnight at 37° C. in 5% $CO_2$, the bacteria harvested and washed three times in PBS. The concentration was estimated by measuring the optical density at 405 mm and was confirmed by counting colony forming units (CFU) of the overnight plating of serial dilutions of the inoculum. Mice were sedated with Saffan administered intravenously. A 20 μl bolus inoculum of live *B. catarrhalis* in PBS was introduced into the lungs as described for IT boosts. Mice were killed by an intra peritoneal injection of pentobarbital sodium either 4 hours after infection or as indicated. Blood was obtained by heart puncture and allowed to clot for collection of serum. The trachea was exposed through the neck and bronchoalveolar lavage (BAL) was obtained by instilling and recovering 0.5 ml of PBS into the lungs via a cannula. After obtaining the BAL, the intact lungs were excised, placed in a 2 ml volume of PBS, and homogenised in a tissue homogeniser (9500 rpm; Heidolph DIAX 600, Electro GmbH & Co, Kelheim, Germany). The BAL and the lung homogenate were assessed for bacterial clearance by plating of serial dilutions for CFU determination. Serum was separated by centrifugation at 4° C. and 450×g for 10 min (Juoan BR3.11, St Nazaire, France) and stored at −80° C.

Results

Mice were immunized IPP and were boosted IT with purified protein. The data shown in FIG. 4 shows the percentage of enhanced clearance of bacteria in either the bronchoalveolar lavage (BAL) or the lung tissue, compared to non-immune bacterial recovery.

A protein with an apparent molecular mass of 71 kDa was most effective at enhancing clearance from the BAL, but the immune response to this protein was less effective in clearance from lung tissue.

The immune response following immunization with a protein with an apparent molecular mass of 44 kDa was effective at clearing bacteria from both the BAL and lung tissue. Immunisation with 15 and 30 kDa proteins showed greater than 50% enhanced clearance in both BAL and lung, whereas a 14.5 kDa protein that showed this for the BAL clearance, did not achieve the same protection in the lung. A 14 kDa protein was not effective in clearing bacteria in the BAL but was able to slightly enhance clearance from the lung.

The invention claimed is:

1. An isolated immunogenic, outer membrane protein of the bacteria *Branhamella* (*Moraxella*) *catarrhalis*, wherein said outer membrane protein is selected from the group consisting of an isolated, immunogenic *Branhamella* (*Moraxella*) *catarrhalis* protein that has an apparent molecular mass of 14, 14.5, 15 or 35 kDa as determined by SDS-PAGE wherein said protein is isolatable from said bacteria using an extraction procedure that comprises a zwittergent extract of a broth culture of said bacteria, followed by ion exchange chromatography of said extract on a Q2 column, and one or more preparative gel electrophoresis elutions of said ion exchange column's fractions that contain said immunogenic protein, wherein said one or more preparative gel electrophoresis elutions are performed under conditions that separate the proteins that are being eluted into at least two fractions based on a protein's molecular mass, and selecting the fraction(s) that contain the protein that has the desired molecular mass,
   (a) wherein mice immunized with said 14 kDa protein and challenged with said bacteria have an enhanced clearance of said bacteria from their lungs as compared to that of non-immunized mice;
   (b) wherein mice immunized with said 14.5 kDa protein and challenged with said bacteria have an enhanced clearance of said bacteria in brochoalveolar lavage as compared to that of non-immunized mice;
   (c) wherein mice immunized with said 15 kDa protein and challenged with said bacteria have an enhanced clearance of said bacteria from both a bronchoalveolar lavage and their lungs as compared to that of non-immunized mice; and
   (d) wherein said protein with said apparent molecular mass of 35 kDa comprises the following N-terminal sequence: TPTVYGKAFLTIDANNTDXTY (SEQ ID NO:3).

2. The isolated protein of claim 1 wherein said protein is said isolated protein that has an apparent molecular mass of 14 kDa.

3. The isolated protein of claim 1 wherein said protein is said isolated protein that has an apparent molecular mass of 14.5 kDa.

4. The isolated protein of claim 1 wherein said protein is said isolated protein that has an apparent molecular mass of 15 kDa.

5. The isolated protein of claim 1 wherein said protein is said isolated protein that has an apparent molecular mass of 35 kDa.

6. A protein preparation comprising an isolated immunogenic, outer membrane protein of the bacteria *Branhamella* (*Moraxella*) *catarrhalis* that has an apparent molecular mass of 20 kDa as determined by SDS-PAGE, and that has the N-terminal sequence:
   AISYGNSADAQPYVGAKIGQVDAKQINNKNT (SEQ ID NO:1) wherein, based on SDS-PAGE migration, said preparation lacks *Branhamella* (*Moraxella*) *catarrhalis* proteins that have an apparent molecular mass of 30 kDa and higher.

7. A protein preparation comprising an isolated, immunogenic, outer membrane protein of *Branhamella* (*Moraxella*) *catarrhalis* that has an apparent molecular mass of 20 kDa as determined by SDS-PAGE and has the N-terminal sequence: AISYGNSADAQPYVGAKIGQVDAKQINNKNT (SEQ ID NO:1) wherein said protein that has an apparent molecular mass of 20 kDa is producible by a process comprising:

(a) growing a culture of *Branhamella* (*Moraxella*) *catarrhalis* bacterial cells, (b) washing said bacterial cells by suspending said cells in phosphate buffered saline (PBS) and centrifuging at 4° C. to pellet said cells;

(c) extracting outer membrane proteins from the washed bacterial cells by the addition of a zwittergent and subsequent ethanol precipitation;

(d) purifying said 20 kDa outer membrane protein by ion exchange chromatography of the extracted outer membrane proteins of part (c) on an ion exchange column that has an ion exchange like that of a Q2 column and pooling the fractions that contain said 20 kDa protein; and (e) purifying said protein by preparative gel electrophoresis under conditions that separate the proteins that are being eluted into at least two fractions based on a protein's molecular mass, and selecting the fraction(s) that contain the protein that has an apparent molecular mass of 20 kDa;

wherein, based on SDS-PAGE migration, said preparation lacks *Branhamella* (*Moraxella*) *catarrhalis* proteins that have an apparent molecular mass of 30 kDa and higher.

* * * * *